(12) United States Patent
Kuwahara et al.

(10) Patent No.: US 8,243,275 B2
(45) Date of Patent: Aug. 14, 2012

(54) OPTICAL MEASUREMENT APPARATUS AND OPTICAL MEASUREMENT METHOD FOR A LIQUID OR MOLTEN MATERIAL

(75) Inventors: Masashi Kuwahara, Tsukuba (JP); Toshio Fukaya, Tsukuba (JP); Takayuki Shima, Tsukuba (JP); Junji Tominaga, Tsukuba (JP); Rie Endo, Tokyo (JP); Masahiro Susa, Tokyo (JP); Michio Suzuki, Tokyo (JP); Koichi Tsutsumi, Tokyo (JP)

(73) Assignees: National Institute of Advanced Industrial Science and Technology, Tokyo (JP); J. A. Woolam Japan Corporation, Tokyo (JP)

( * ) Notice: Subject to any disclaimer, the term of this patent is extended or adjusted under 35 U.S.C. 154(b) by 525 days.

(21) Appl. No.: 12/490,137

(22) Filed: Jun. 23, 2009

(65) Prior Publication Data

US 2009/0323071 A1 Dec. 31, 2009

(30) Foreign Application Priority Data

Jun. 24, 2008 (JP) .................................. 2008-164896

(51) Int. Cl.
*G01N 21/55* (2006.01)

(52) U.S. Cl. ....................................................... 356/445
(58) Field of Classification Search .................... None
See application file for complete search history.

(56) References Cited

U.S. PATENT DOCUMENTS

| 5,572,322 | A | * | 11/1996 | Noda | 356/445 |
| 7,064,837 | B2 | * | 6/2006 | Mori et al. | 356/445 |
| 2003/0189707 | A1 | * | 10/2003 | Naya et al. | 356/445 |

OTHER PUBLICATIONS

Yagi et al., Determination of refractive index and electronic polarisability of oxygen for lithium-silicate melts using ellipsometry, Journal of Non-Crystalline Solids, vol. 315, 2003, pp. 54-62.

* cited by examiner

*Primary Examiner* — Gregory J Toatley
*Assistant Examiner* — Amanda Merlino
(74) *Attorney, Agent, or Firm* — Birch, Stewart, Kolasch & Birch, LLP

(57) ABSTRACT

An apparatus for optical measurement of a liquid or molten material, which has: a transparent container which has a bottom face and is capable of containing a to-be-measured material therein, with the bottom face at least having a flat face and being transparent; and an optical device that irradiates a light to the bottom face of the container and that detects and measures a reflected light from the bottom face; and a method for optically measuring a liquid or molten material using the apparatus.

11 Claims, 5 Drawing Sheets

OPTICAL MEASUREMENT APPARATUS AND OPTICAL MEASUREMENT METHOD FOR A LIQUID OR MOLTEN MATERIAL

FIELD OF THE INVENTION

The present invention relates to an optical measurement apparatus and an optical measurement method for a liquid or molten material. In particular, the present invention relates to an apparatus for optically measuring a liquid or molten material, and to a noncontact optical measurement method for a molten material, in each of which method and apparatus light is irradiated to the liquid or molten material, to thereby measure physical properties, such as refractive index, reflectivity, or absorptance, of the material.

BACKGROUND OF THE INVENTION

In recent years, physical properties of a liquid or molten material are utilized in various fields. For example, in data storage and accumulation fields, such as an optical disk and a phase-change memory, the material is used that is obtained by heating a raw material to thereby melt and then solidify it. In a refining process, the material is directly melted at high temperature, to thereby manufacture a steel product and the like. Further, a liquid-state material, such as liquid crystal, is also used, to constitute a display surface of a image (graphic) display device and the like.

As described above, the physical properties of a liquid or molten material have important factors and functions in various fields. However, the measurement of the physical properties of a liquid or molten-state material is not conducted so often currently because the measurement involves various difficult disadvantages. For example, in the case where the material is in a molten state, the surface of the liquid material that is subjected to the surrounding mechanical vibration, is ruffled. In other words, the liquid material is exposed to an inappropriate condition even under an optical measurement having a characteristic of a noncontact and nondestructive measurement.

In particular, in the case of a material at high-temperature, since it is required to avoid the damage of a measurement instrument due to the high temperature, it is difficult to measure the physical properties by bringing the to-be-measured material to contact with a general sensor or probe. In contrast with this, an optical measurement enables a noncontact and nondestructive measurement. It is possible to measure an object at a distance where no influence by high temperature of the object is caused, because light can be used in the optical measurement. Thus, the optical measurement may be appropriately used in measurement at high temperature.

As an apparatus using this characteristic of the optical measurement, an apparatus is reported in Journal of Non-Crystalline Solids, vol. 315 (2003) 54. According to this apparatus, monochromatic ellipsometry is combined with a heating furnace, to conduct an optical constant measurement of a high-temperature material.

An optical measurement using ellipsometry will be described below. The ellipsometry is a measurement apparatus using polarization of light. The ellipsometry may be simply described as follows. When a certain linear polarization is caused to enter a material to be measured (which is also called "to-be-measured material") and is reflected from the material, the linear polarization is converted to elliptic polarization. Then, the phase of the elliptic polarization and the polarization degree are measured. Since those reflect the optical information of the to-be-measured material, the thus-reflected light can be analyzed, to determine an optical constant.

The monochromatic ellipsometry is a measurement to use monochromatic light to measure an optical constant, i.e. a refractive index. Generally, He—Ne laser is used, whose wavelength is 632·8 nm. In this case, the optical constant of the molten material only to this wavelength is measured. In contrast with this, spectroscopic ellipsometry using various wavelengths can provide a measurement of light in a wide range from ultraviolet light (wavelength of 250 nm) to far-infrared light (wavelength of 30 μm).

SUMMARY OF THE INVENTION

As described above, although the optical measurement of a liquid or molten material has advantages not achievable by other mechanical measurements, the optical measurement of a liquid or molten material is involved with disadvantages such as the vibration or ruffling of the measuring surface, which have been required to be solved. In particular, in the case of a measurement at high temperature, another new disadvantage different from the above ones also appears remarkably. Generally, a substance comes to have high chemical reactivity and initiate various reactions when a temperature comes high. For example, there is a disadvantage due to evaporation. Specifically, due to the evaporation at a temperature higher than the boiling point as well as a strongly decrease in mass of the substance, such disadvantages are caused as dissipation of the material and contamination of the measurement apparatus due to the evaporated substance. Chemical reaction also comes to be a significant disadvantage. Specifically, heating of a material in the air makes the material to tend to easily bond with oxygen or nitrogen in the air, thus causing a change in the properties of the material. In this case, the material changes to another material utterly different from the original one which is to be measured. Thus, it is necessary to avoid this.

Some disadvantages have been also pointed out, with regard to the optical constant measurement method of a high-temperature material, according to Journal of Non-Crystalline Solids, vol. 315 (2003) 54. One is that the material is required not to initiate reactions such as evaporation or oxidation at high temperature. This limits measurement objects to very special materials. Another important point is that a relatively large amount of the material is required as a to-be-measured material. The optical measurement generally requires a flat surface. In order to realize the flat face, in the above method, a large amount of the material is melted, to utilize a phenomenon that such molten material has a flat upper surface due to the gravity. However, unlike a solid matter, a molten material tends to have a round surface due to the surface tension. Thus, a small amount of a molten material consequently has a spherical surface. When light is irradiated to the spherical surface, the reflected light is scattered in all directions or is reflected in an angular direction different from that in the case of secular reflection. In order to realize a surface that is not spherical but is flat, a large amount of material is required.

The above method and apparatus can achieve a measurement of such a material that is stable at high temperature and that is low in cost. However, a material to be used for, for example, data storage and an accumulation medium, is unstable at high temperature and is relatively high cost. Therefore, the above method and apparatus are disadvantageous in the application scope and cost.

The present invention is contemplated for providing an optical measurement apparatus and a measurement method for measuring physical properties of a liquid or molten material, by which the above-described various disadvantages are eliminated and even a small amount of the liquid or molten material as a measurement object can be readily subjected to an optical measurement with a flat measuring surface, without causing evaporation of the to-be-measured material or reaction of it with other substances.

Herein, generally, the term "optical constant measurement" has the same meaning of a refractive index measurement (both of real part and imaginary part). On the other hand, the term "optical measurement" in the present invention means to include not only such an optical constant measurement but also an optical constant measurement including a reflectivity measurement and an absorptance measurement.

According to the present invention, there are provided the following means:

(1) An apparatus for optical measurement of a liquid or molten material, which comprises:
a transparent container which has a bottom face and is capable of containing a to-be-measured material therein, with at least the bottom face having a flat face and being transparent; and
an optical device (i.e. an optical system) that irradiates a light to the bottom face of the container and that detects and measures a reflected light from the bottom face.

(2) The apparatus as described in the above item (1), which has a heating furnace for melting the to-be-measured material, with the to-be-measured material being composed of a substance that is solid at room temperature.

(3) The apparatus as described in the above item (1) or (2), wherein the optical device has an incident-side optical-path-redirecting means for irradiating a light from a light source to the bottom face of the container.

(4) The apparatus as described in the above item (1) or (2), wherein the optical device has a reflection-side optical-path-redirecting means for irradiating a light reflected from the to-be-measured material via the bottom face of the container to a photodetector.

(5) The apparatus as described in the above item (3), wherein the incident-side optical-path-redirecting means is a mirror or a total reflection prism.

(6) The apparatus as described in the above item (4), wherein the reflection-side optical-path-redirecting means is a mirror or a total reflection prism.

(7) The apparatus as described in the above item (1) or (2), wherein the container is a vacuum container that does not alter the to-be-measured material and that is resistant to the to-be-measured material.

(8) The apparatus as described in the above item (1) or (2), wherein the container is sealed with an inactive gas that does not alter the to-be-measured material and that is resistant to the to-be-measured material.

(9) The apparatus as described in the above item (1), (2), (7), or (8), wherein the container is a quartz-made container that is resistant to a temperature up to 1,200° C.

(10) The apparatus as described in the above item (1), (2), (7), (8), or (9), wherein the bottom face of the container has a surface roughness that is equal to or lower than a wavelength of a measurement light of the optical device.

(11) A method for optically measuring a liquid or molten material, which comprises the steps of:
providing a to-be-measured material, to put in a transparent container that has a flat bottom;
irradiating a measurement light to enter a bottom face of the transparent container; and
detecting and measuring a reflected light component from the to-be-measured material in a liquid or molten state, among reflected lights of the measurement light.

(12) The method as described in the above item (11), wherein the to-be-measured material is solid at 20° C., wherein, after the providing step, the to-be-measured material put in the transparent container is heated to melt, and wherein, in the detecting and measuring step, the reflected light component from the to-be-measured material in the molten state is detected and measured.

(13) The method as described in the above item (11) or (12), wherein the transparent container further contains therein a material that is more easily oxidized than the to-be-measured material in a liquid or molten state, in a state separated from the to-be-measured material in a liquid or molten state.

According to the present invention, in the optical measurement of a liquid or molten material, the measuring surface is set at a bottom face of the liquid or molten material as a to-be-measured object, to thereby readily generate a flat specular surface that can be stably measured. Further, the measurement at the bottom face of the liquid or molten material can realize a flat face at the bottom face of a transparent container, thereby eliminating the need for a large amount of the to-be-measured material. Furthermore, the liquid or molten material is prevented from causing a reaction with oxygen or nitrogen remaining in the container. Resultantly, many advantages are provided, such as prevention of lowering of the measurement accuracy.

(Action)

According to the measurement apparatus and the measurement method of the present invention, a flat part of a bottom face of a transparent container can be used as an optical measuring surface, to thereby effectively measure even a small amount of the measurement object material. Further, the material is sealed in a transparent and resistant container and the inside of the container can be vacuumized or sealed with an inactive gas. This consequently prevents the liquid or molten-state material from evaporating or causing a reaction with other substances such as oxygen or nitrogen. Furthermore, by allowing the container to contain therein, together with the measurement object material, a substance (e.g., titanium) that more easily reacts with other substance than the material as a measurement object and that has a melting point higher than that of the material, such a substance can be disposed while being easily separated from the material as a measurement object, thus realizing a stable optical measurement of the liquid or molten material at low cost.

Other and further features and advantages of the invention will appear more fully from the following description, appropriately referring to the accompanying drawings.

DETAILED DESCRIPTION OF THE INVENTION

The optical measurement apparatus and the optical measurement method of a liquid or molten material according to the present invention will be explained based on the following embodiments, appropriately referring to the accompanying drawings.

Embodiment 1

Figure 1:
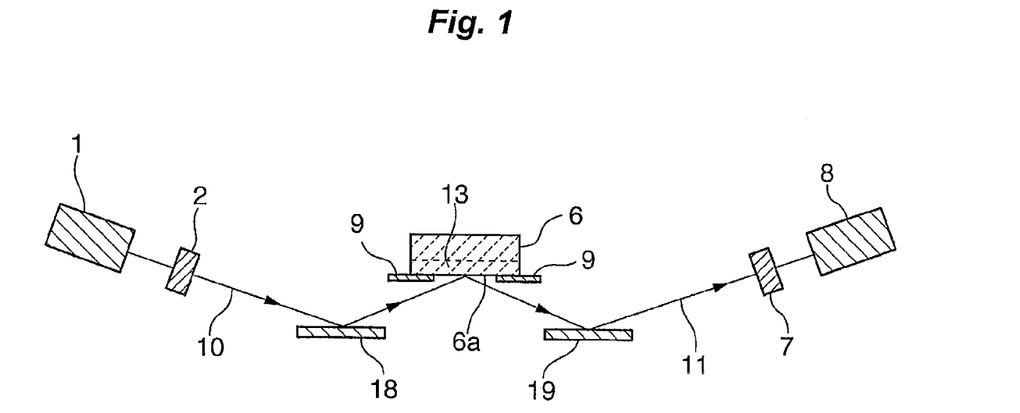
FIG. 1 is a schematic side cross-sectional view illustrating an optical measurement apparatus according to Embodiment 1 of the present invention.

FIG. 1 is a schematic side cross-sectional view illustrating an optical measurement apparatus of a liquid or molten material according to Embodiment 1 of the present invention. In the optical measurement apparatus of Embodiment 1, the measurement of a refractive index of the molten material using ellipsometry will be described as a main measurement item, but the present invention may also be applied not only to the measurement of a refractive index but also to other measurements of an optical constant, such as a measurement of a reflectivity or a measurement of an optical absorptance, in the similar manner.

A transparent container 6 for containing therein a liquid or molten material 13 is entirely formed of a transparent material in Embodiment 1, and the bottom of the container has a bottom face 6a of a flat face having smoothness required for an optical measurement. The container 6 is made of a material that does not alter the to-be-measured material and that is resistant to the to-be-measured material. When setting that light has a wavelength $\lambda$, the smoothness of the container bottom face 6a can be represented by the roughness of the surface from about $\lambda$ to about $\lambda/10$. When the container bottom face 6a does not have this smoothness, a case may be caused where light is scattered significantly and thus a reliable measurement is impossible.

The material of the transparent container 6 is most preferably quartz, but also may be other transparent materials. For example, the transparent container 6 may be made of optical glass material, such as BK-7. However, in this case, the highest temperature of the optical glass material can resist is 400 to 500° C. When the optical glass material is in a temperature region higher than 400 to 500° C., then the temperature exceeds the glass transition point, to thereby cause a deformation of the shape of the container itself, thus making it impossible to use the material. Furthermore, unlike quartz glass, such optical glass material is added with various impurities (e.g., alkali metal such as sodium, or transition metal such as iron), and thus a risk is caused where these substances added may be diffused or dissolved in the molten material at high temperature. In this case, another risk is caused where the molten material itself may alter to another material. However, no disadvantage is caused when the material i.e. the object substance, is liquid at an ordinary temperature or the material is used at the highest temperature of about 300° C.

The transparent container 6 containing the to-be-measured material is placed on a sample stand 9. The sample stand is shaped so that a hole is opened at the center, and a measurement light can be irradiated therethrough to the bottom face of the container. In this layout, an optical measurement can be achieved, by irradiating light to enter the bottom face of the container 6 containing therein a substance in a liquid state at an ordinary temperature.

Figure 2:
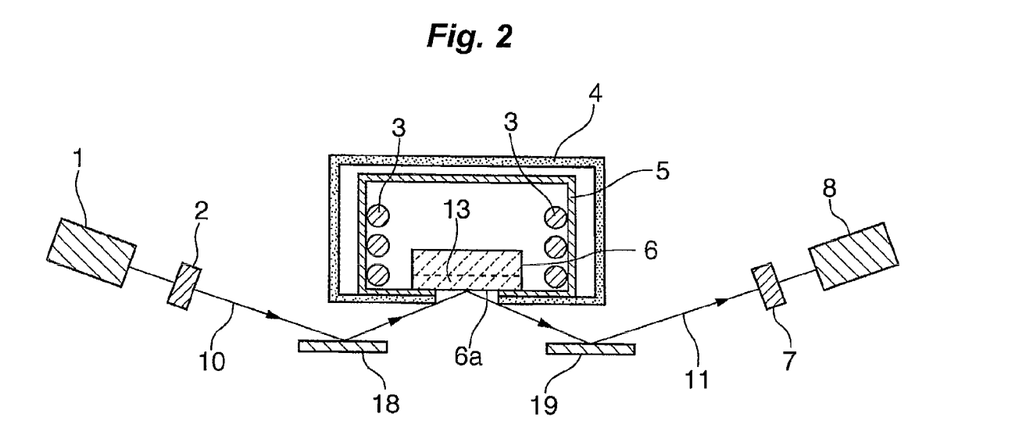
FIG. 2 is a schematic side cross-sectional view illustrating an optical measurement apparatus including a heating furnace according to Embodiment 1 of the present invention.

When the material is melted at high temperature, as shown in FIG. 2, the transparent container 6 containing the to-be-measured material is placed in a heating furnace 5. The heating furnace 5 is structured so that a face on which the container is placed is partially opened. Thus, a bottom face 6a of the container 6 is partially exposed to the outside from the lower part of the heating furnace 5. The heating furnace 5 is made of a heat-resistant material, such as heat-resistant brick or ceramic wool, and includes therein a heat-generating body 3, to thereby achieve heating in a range from the room temperature to about 1,200° C. A heating source may be a means, such as resistance heating, high-frequency heating, or infrared heating. In the case of the resistance heating, the furnace includes therein a resistance heating body (e.g., nichrome wire, tungsten wire, tantalum wire) through which current is caused to flow, to thereby generate heat to heat the inside of the furnace. In the case of the high-frequency heating, the molten material as a measurement object is limited to an electroconductive substance. In this case, the molten material is heated by generating inductive current in the material by the coil to subsequently generate Joule heat by the inductive current flowing in the molten material. In the case of the infrared heating, the molten material is heated by irradiation of infrared ray to the material, to allow the infrared ray to be absorbed by the molten material. There is no particular limit to the present invention, and any of these methods can be applied to the present invention, and it is possible to select a method optimal for the molten material.

Depending on the size of a heating source, a risk may be caused where heat radiated from the heating source heated to about 1,000° C. to the surrounding area causes the breakage of the optical measurement apparatus or the burn injury of an operator for measuring. In order to avoid those, the outer side of the heating furnace 5 is covered by a water-cooling jacket 4. In the case where the heating source is heated up to about 500° C., such a disadvantage is prevented from being caused, without using a water-cooling means, by securely providing heat insulation.

In the present invention, the optical device is utilized to irradiate (project) light to the bottom face of the liquid or molten material 13 contained in the transparent container 6, and the reflected light reflected therefrom is detected to perform measurement. Thus, the light source of the optical device may be placed at a position in an obliquely downward direction of the container, and a light-receiving section for the reflected light may be placed at a position under the container at the opposite side of the light source. However, in an actual case, this layout is disadvantageous in that an optical adjustment is required, the heating furnace is provided at a position higher than those of the light source and a photodetector, and a safety aspect may be insecure. To avoid the disadvantages, in Embodiment 1, optical-path-redirecting means 18 and 19 are provided under the container 6. The optical path of an incident light 10 from a light source 1 is redirected by the optical-path-redirecting means 18, to irradiate a light to the container bottom face 6a, and the reflected light 11 is also received by a photodetector 8 via the optical-path-redirecting means 19. In FIG. 1, the reference numeral 2 denotes a polarizer provided at the light source-side, and the reference numeral 7 denotes an analyzer provided at the photodetector 8-side.

As shown in FIG. 1, a pair of mirrors are provided under the container, as the optical-path-redirecting means 18 and 19 at the incident side and at the reflection side, respectively. In this case, a usable mirror body is limited. In Embodiment 1 of the present invention, the mirror body made of very stable noble metal such as gold or platinum, is used as the mirror body.

Generally, this type of optical-path-redirecting mirror body is formed by an aluminum plate having a surface coated by transparent dielectric material or organic matter. Although this covering material can avoid the oxidation of the surface of the aluminum plate, this covering material causes the loss of information owned by light (information owned by the reflected light from the molten material, in particular). Thus, such a covered mirror is inappropriate for the optical-path-redirecting mirror body. However, an uncovered aluminum mirror, on the other hand, has thereon an oxidized film growing with the lapse of time. This oxidized film also causes the loss of light-related information, thus failing to provide an accurate measurement. Due to the reason as described above, a noble metal mirror free from oxidation is used in Embodiment 1.

Modification Example 1

Figure 3:
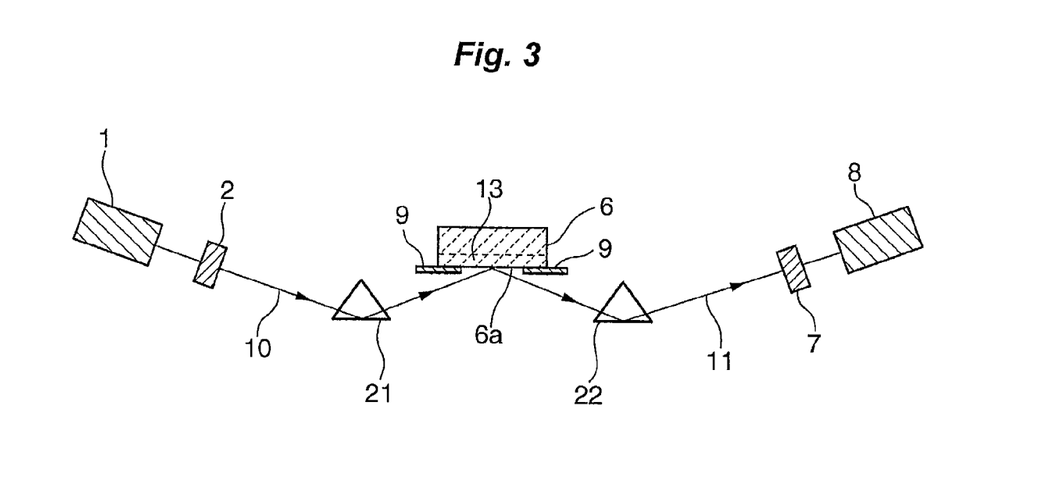
FIG. 3 is a schematic side cross-sectional view illustrating an optical measurement apparatus according to one of modification examples of Embodiment 1 of the present invention.

A noble metal mirror body made of gold, platinum or the like, is stable in the air, and has a favorable light reflectivity. However, such a noble metal mirror body is prepared for an exclusive use through a special manufacture process, and thus requires a high cost. To solve this, in Modification Example 1 of Embodiment 1, a configuration as shown in FIG. 3 is used where prisms 21 and 22 are used as the optical-path-redirecting means instead of the mirror. The total (internal) reflection properties of these prisms 21 and 22 are utilized to provide the same optical-path-redirecting action as that by the mirror. In the case of the prisms 21 and 22, the incident light 10 is caused to enter the bottom face 6a of the container 6 without losing the information thereof, and the reflected light 11 also can be guided to the photodetector 8 while retaining the information thereof. Although the information of light may be changed in some cases, the information of light is changed with regularities. Thus, the regularities can be understood in advance so that the change can be removed at the time of analysis.

In the configuration as described above, when the to-be-measured material is composed of a substance which is liquid at room temperature (20° C.), the to-be-measured material is placed in the transparent container 6 having the flat and smooth bottom face. Then, the incident light 10 entered from the light source 1 via the polarizer 2 is redirected by the mirror body 18 (FIG. 1) or the prism 21 (FIG. 3). Then, the redirected light is irradiated to the liquid 13 via the container bottom face 6a. The reflected light 11 is similarly redirected by the other mirror 19 or prism 22. Then, the redirected light is received by the photodetector 8 via an analyzer 7, thereby performing measurement.

Figure 4:
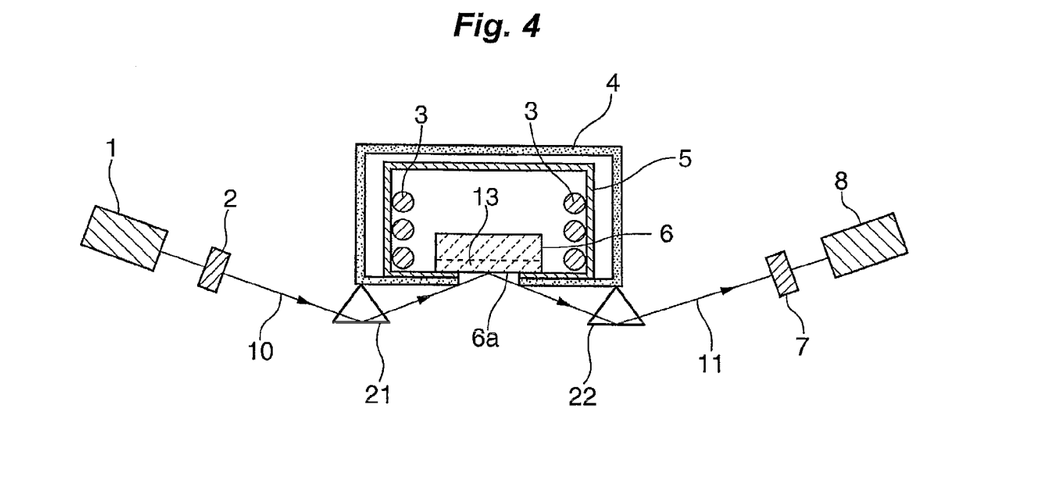
FIG. 4 is a schematic side cross-sectional view illustrating an optical measurement apparatus including a heating furnace according to one of modification examples of Embodiment 1 of the present invention.

Further, when the to-be-measured material is composed of a substance which is solid at room temperature (20° C.), the to-be-measured material is placed in the transparent container 6 having the flat and smooth bottom face. Then, since the to-be-measured material requires heating, the material is heated to a molten-state, which is different from the case of placing the material in a liquid state at the ordinary temperature as it is in the container. Then, the incident light 10 entered from the light source 1 via the polarizer 2 is redirected by the mirror body 18 (FIG. 2) or the prism 21 (FIG. 4). Then, the redirected light is irradiated to the liquid and molten material 13 through the container bottom face 6a. Then, the reflected light 11 is similarly redirected by the other mirror 19 or prism 22. Then, the redirected light is received by the photodetector 8 via the analyzer 7, to perform measurement.

As described above, the to-be-measured material is contained in the container 6, and is optionally heated to be molten. If required, the molten material is sealed in the container 6 in a vacuum manner. This is for the purpose of preventing the molten material that generally has a high chemical activity, from causing reduction in the amount thereof due to the evaporation or from causing contamination to the apparatus. Some materials also may bond to oxygen or nitrogen in the air, to cause a violent chemical reaction therewith. In particular, when a chalcogenide (a compound or alloy formed, for example, of antimony (Sb) or tellurium (Te)) that is used for a recording material of an optical disk, is melted in the air, the chalcogenide violently cause oxidation and/or evaporation. To prevent this reaction, it is necessary to provide the container 6 as a vacuum container.

Modification Example 2

In Modification Example 2 of Embodiment 1, when the molten material 13 is sealed in the container 6, it is possible to contain in the inside of the container together with an inactive gas, without using vacuumization. In this case, the inside of the container is vacuumized in advance, and then the inactive gas is introduced in the container. Generally, inactive gases do not decompose or cause reaction with other substances. Thus, no risk is caused where the molten material 13 reacts with the inactive gas to alter or be changed into another substance. Examples of the inactive gas that can be used include helium, argon, xenon, krypton, or the like, but among which argon is most preferable from the viewpoints of availability and cost.

Embodiment 2

Figure 5:
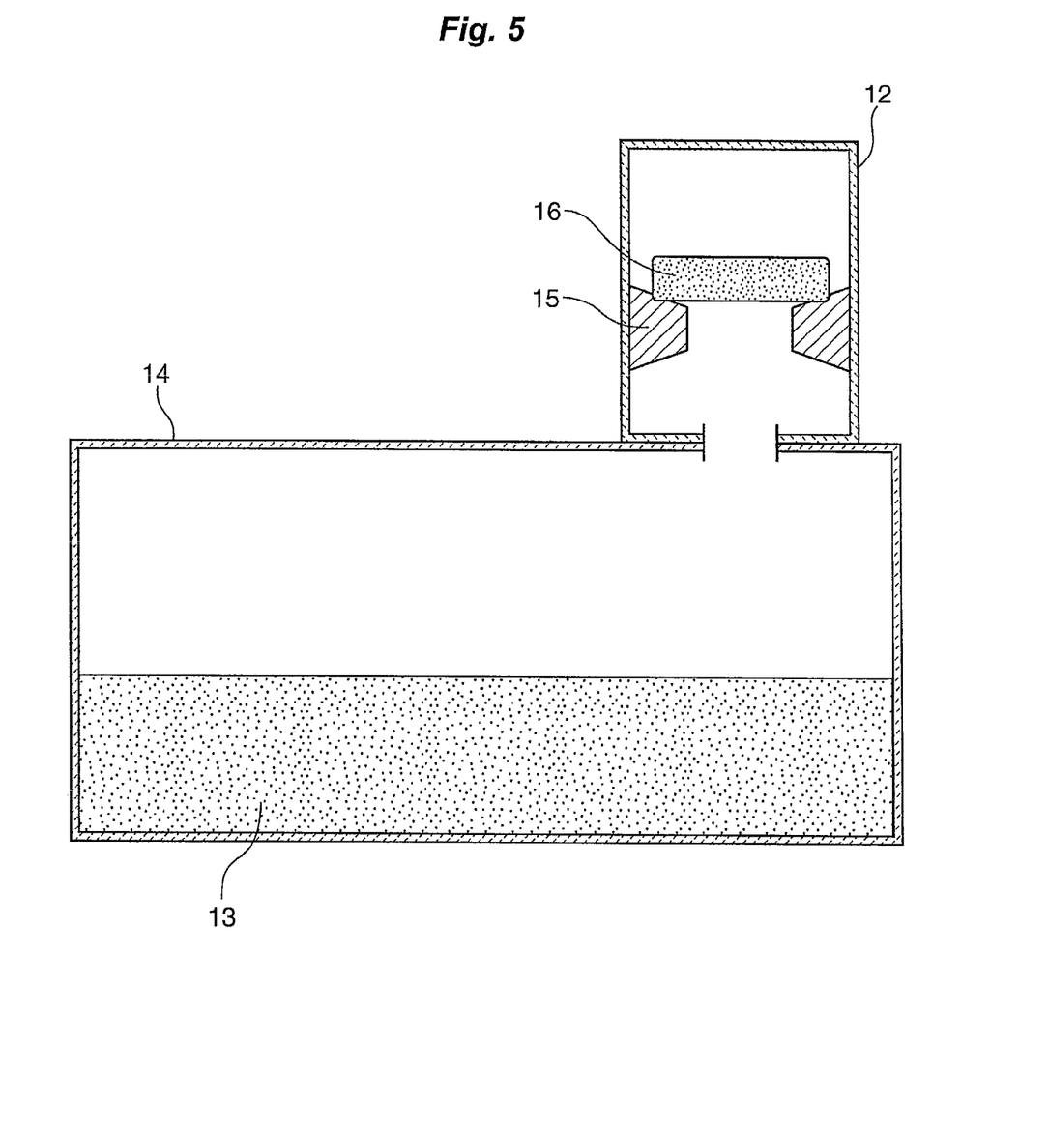
FIG. 5 is a schematic side cross-sectional view illustrating a transparent container according to Embodiment 2 of the present invention.

As described above, the molten material must be sealed in the container, in order to prevent the molten material from evaporating and from reacting with other substances. In order to further prevent the material from altering due to the reaction, a reducing agent may be additionally contained in the container. FIG. 5 is a cross-sectional view illustrating a transparent container 14 according to Embodiment 2 of the present invention. In Embodiment 2, a special room 12 is provided on the container 14 so that the other room 12 communicates with the space in the container 14. The other room 12 has therein a supporting section 15 for a reducing agent. On this supporting section 15, a highly-active substance 16 as reducing agent is placed. Further, if possible, it is preferred to use the highly-active substance 16 contained in the container in combination with sealing under vacuumization or sealing with an inactive gas. The reason is that a small or trace amount of oxygen or nitrogen generally remains in the container, even when the inside of the container is vacuumized or is sealed with an inactive gas.

In Embodiment 2, in order to prevent these remaining substances from causing reaction with the molten material 13, the remaining oxygen or nitrogen is in a positive way allowed to react with the highly-active substance 16, to thereby cause the remaining substance such as oxygen or nitrogen to disappear. In this case, as the highly-active substance 16, it is necessary to select a substance that more easily cause reaction with oxygen or nitrogen than the molten material 13 of a measurement object. Typical examples of the highly-active substance 16 highly reactive than the molten material 13, include alkaline earth metals and transition metals. In particular, magnesium or titanium is most preferable, from the viewpoints of availability and cost.

Embodiment 3

Figure 6:
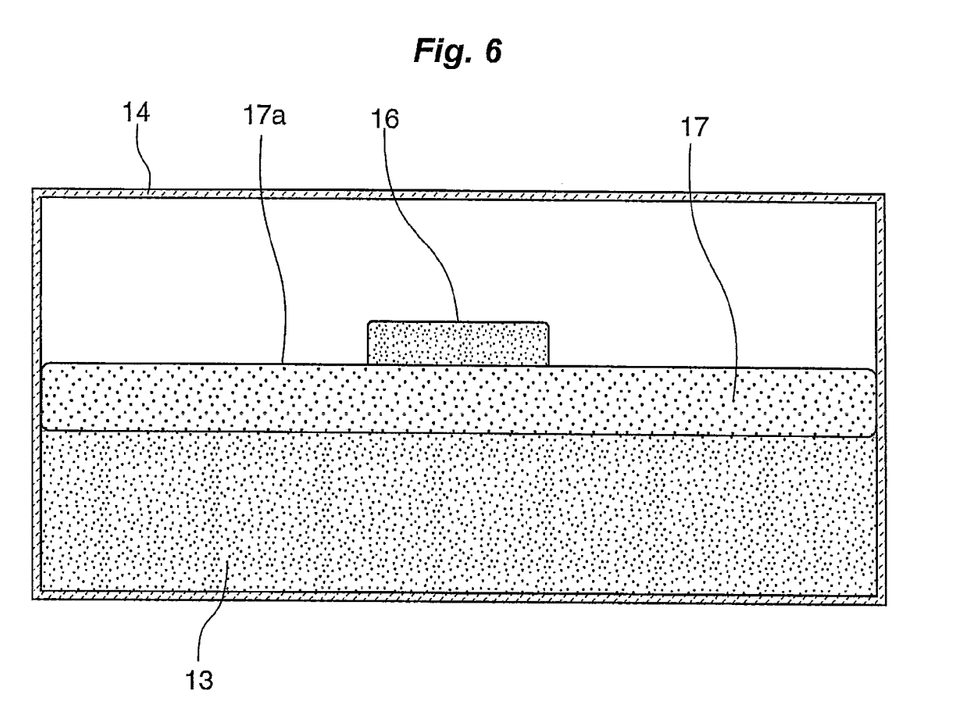
FIG. 6 is a schematic side cross-sectional view illustrating a container in which a molten material is sealed according to Embodiment 3 of the present invention.

FIG. 6 is a cross-sectional view illustrating a container in which the molten material is sealed according to Embodiment 3 of the present invention. In Embodiment 3, on the upper face of the heated molten material 13 contained in the transparent container 14, a substance 17 is placed that has a smaller specific gravity than that of the molten material 13, that has a higher melting point than that of the molten material 13, and that is stable at high temperature. Further, on the upper face 17a, the highly-active substance 16 as a reducing agent is placed. As the substance 17 that is to be placed on the upper face of the molten material 13, that is small in specific gravity and stable at high temperature, use may be made, for example, of ceramic wool, or the like. The reducing agent may be selected from a substance that causes more easily reaction with oxygen or nitrogen than the molten material 13. Oxygen and nitrogen remaining in the container are allowed to react with the highly-active substance 16 functioning as a reducing agent, without being brought into contact with the molten material 13, which results in no existence thereof as an elementary substance. This can perfectly prevent the alteration of the molten material 13 due to its reaction with the remaining substance, thus achieving a stable and reliable optical measurement.

The Embodiment 2 and Embodiment 3 can be applied to the optical measurement according to the present invention in the same manner as the Embodiment 1 and Modification Examples 1 and 2 as well as the explanatory figures of FIGS. 1 to 4, except that the container 14 and the bottom face thereof (14a, not shown) are changed to the container 6 and the bottom face 6a thereof, respectively.

Figure 7:
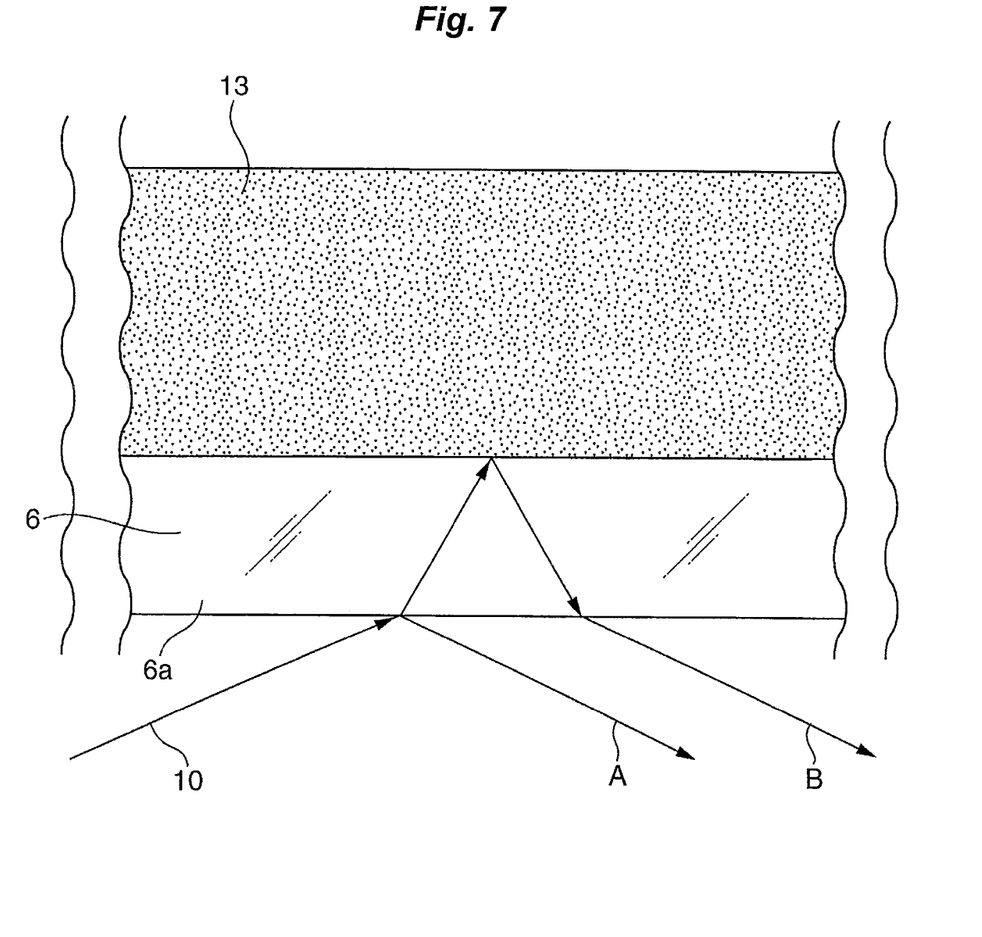
FIG. 7 is an enlarged view illustrating an optical path (or a ray diagram) of the incident light and the reflected light at the bottom of a transparent container in an optical measurement apparatus of the present invention.

FIG. 7 is an enlarged view illustrating the optical path of the incident light and the reflected light at the bottom of the transparent container in the optical measurement apparatus of the present invention. In the present invention, the liquid or molten material is measured through the bottom face of the container in the state contained in the container. Thus, the incident light 10 from the light source is irradiated to the liquid or molten material via the bottom face of the container. Thus, when the reflected light as it is in this layout is measured, the thus-measured light is affected by the container. In other words, the reflected light 11 includes: the reflected light A that does not reach the liquid or molten material 13, and that is reflected at the bottom face 6a of the container 6; and the reflected light B that reaches the liquid or molten material 13 via the bottom of the container, and that is reflected at the container bottom. The necessary measurement light is a light including the information regarding only the liquid or molten material 13. Thus, in the present invention, it is required to extract, from the above-mentioned reflected lights, a reflected light component only including the information regarding the liquid or molten material 13, so that the thus-extracted light can be detected by the photodetector to measure the physical properties of the material.

The reflected light A does not include the information regarding the liquid or molten material 13 at all, and has only the information regarding the container 6. Thus, this reflected light A must be excluded at the time of measuring. In this case, with respect to a certain incident light 10, the reflected light A and the reflected light B are reflected at different cites at the container bottom face 6a. Thus, the reflected light A can be excluded, by adjusting the position of the photodetector so as to receive only the reflected light B. Alternatively, as another method, use may be made of a shielding plate (not shown) to provide for shielding the reflected light A in the optical path of said reflected light A.

The reflected light B includes the optical information regarding the to-be-measured liquid or molten material 13 and the optical information regarding the container 6. In this case, the transparent container can be made of a constituting material whose optical constant is known in advance, or alternatively, the optical constant of the transparent container 6 can be determined prior to the measurement. Thus, using the above-mentioned transparent container whose optical constant is known or can be determined, the optical information regarding the container 6 from the reflected light B can be extruded or remove at the measurement. Examples of the constituting material of the container whose optical constant is known in advance, include quartz. Quartz has an optical properties measured in a wide range of wavelength. Thus, when quartz is used as the container material, the optical information regarding quartz, i.e. the optical information of the container, can be easily removed from the reflected light B.

In the cases of the Embodiment 2 and Embodiment 3, the container 14 and the bottom face thereof (14a, not shown) are applied for the container 6 and the bottom face 6a thereof, respectively, in the above explanation of FIG. 7.

As described above, according to the present invention, instead of irradiating a light to a liquid or molten material from the upper face-side of the container containing therein the liquid or molten material, a light is irradiated from the container bottom face-side to perform an optical measurement. Thus, by the use of the container having a flat bottom face, a flat face of the liquid or molten material is formed at the bottom of the container by the gravity independently from the surface tension. Resultantly, according to the present invention, a light having entered this face has specular reflection and is received by the photodetector. When measurement is made from the upper face of the liquid or molten material, a large amount of said liquid or molten material must be placed in the container in order to form a flat upper face. In contrast with this, according to the present invention, even in a small amount of the liquid or molten material placed in the container, a flat face of the liquid or molten material can be effectively formed at the container bottom. In the case of a substance that is melted at high temperature, the present invention can advantageously exhibit a readily and accurate optical measurement, by sealing the molten material in the container in a vacuum manner, or by sealing it together with a substance that is easily causing a reaction with the remaining oxygen or nitrogen in a manner separated said substance from the molten material.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2008-1164896 filed in Japan on Jun. 24, 2008, which is entirely herein incorporated by reference.

What we claim is:

1. An apparatus for optical measurement of a liquid or molten material, comprising:
   a transparent container which has a bottom face and is capable of containing a to-be-measured material therein, with the bottom face at least having a flat face and being transparent;

an optical device that irradiates a light to the bottom face of the container and that detects and measures a reflected light from the bottom face; and a heating furnace for melting the to-be-measured material, with the to-be-measured material being composed of a substance that is solid at room temperature.

2. The apparatus according to claim 1, wherein the optical device has an incident-side optical-path-redirecting means for irradiating a light from a light source to the bottom face of the container.

3. The apparatus according to claim 2, wherein the incident-side optical-path-redirecting means is a mirror or a total reflection prism.

4. The apparatus according to claim 1, wherein the optical device has a reflection-side optical-path-redirecting means for irradiating a light reflected from the to-be-measured material via the bottom face of the container to a photodetector.

5. The apparatus according to claim 4, wherein the reflection-side optical-path-redirecting means is a mirror or a total reflection prism.

6. The apparatus according to claim 1, wherein the container is a vacuum container that does not alter the to-be-measured material and that is resistant to the to-be-measured material.

7. The apparatus according to claim 1, wherein the container is sealed with an inactive gas that does not alter the to-be-measured material and that is resistant to the to-be-measured material.

8. The apparatus according to claim 1, wherein the container is made of quartz resistant to a temperature up to 1,200° C.

9. The apparatus according to claim 1, wherein the bottom face of the container has a surface roughness that is equal to or lower than a wavelength of a measurement light of the optical device.

10. A method for optically measuring a liquid or molten material, the method comprising the steps of:
providing a to-be-measured material, to put in a transparent container that has a flat bottom;
irradiating a measurement light to enter a bottom face of the transparent container; and
detecting and measuring a reflected light component from the to-be-measured material in a liquid or molten state, among reflected lights of the measurement light,
wherein the to-be-measured material is solid at 20° C., wherein, after the providing step, the to-be-measured material put in the transparent container is heated to melt, and wherein, in the detecting and measuring step, the reflected light component from the to-be-measured material in the molten state is detected and measured.

11. The method according to claim 10, wherein the transparent container further contains therein a material that is more easily oxidized than the to-be-measured material in a liquid or molten state, in a state separated from the to-be-measured material in a liquid or molten state.

* * * * *